US 8,932,269 B2

(12) United States Patent
Dion et al.

(10) Patent No.: US 8,932,269 B2
(45) Date of Patent: Jan. 13, 2015

(54) DISPOSABLE PUMPING SYSTEM AND COUPLER

(71) Applicants: Ernest A. Dion, Danvers, MA (US); Ed McLean, Billerica, MA (US); Fred Boussu, West Newbury, MA (US); Manny J. Salinas, North Andover, MA (US); Sean J. Albert, Barrington, NH (US)

(72) Inventors: Ernest A. Dion, Danvers, MA (US); Ed McLean, Billerica, MA (US); Fred Boussu, West Newbury, MA (US); Manny J. Salinas, North Andover, MA (US); Sean J. Albert, Barrington, NH (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/718,337

(22) Filed: Dec. 18, 2012

(65) Prior Publication Data

US 2013/0202455 A1 Aug. 8, 2013

Related U.S. Application Data

(63) Continuation of application No. 12/644,391, filed on Dec. 22, 2009, now Pat. No. 8,337,175.

(51) Int. Cl.
| | |
|---|---|
| *A61M 1/00* | (2006.01) |
| *F04B 17/00* | (2006.01) |
| *F04B 35/00* | (2006.01) |
| *F04B 7/00* | (2006.01) |
| *F04B 53/14* | (2006.01) |
| *F04B 53/10* | (2006.01) |
| *A61B 17/3203* | (2006.01) |
| *A61B 17/00* | (2006.01) |

(52) U.S. Cl.
CPC ............. *F04B 7/00* (2013.01); *A61B 17/3203* (2013.01); *A61B 2017/00477* (2013.01); *F04B 53/147* (2013.01); *F04B 53/1002* (2013.01)
USPC ............ 604/228; 417/360; 417/415; 604/152

(58) Field of Classification Search
USPC .................. 417/53, 360, 415, 454, 569, 571; 604/228, 151, 152
See application file for complete search history.

(56) References Cited

U.S. PATENT DOCUMENTS

| | | | |
|---|---|---|---|
| 3,530,771 A | 9/1970 | Bowman et al. | |
| 3,628,812 A | 12/1971 | Larralde et al. | |
| 3,684,410 A | 8/1972 | Fitzgerald et al. | |

(Continued)

FOREIGN PATENT DOCUMENTS

| | | |
|---|---|---|
| DE | 3541708 A1 | 5/1987 |
| EP | 470781 A1 | 2/1992 |

(Continued)

OTHER PUBLICATIONS

International Search Report and Written Opinion for International Application No. PCT/US2007/089052, mailed Jul. 25, 2008, 14 pages.

(Continued)

*Primary Examiner* — Peter J Bertheaud
(74) *Attorney, Agent, or Firm* — Fish & Richardson P.C.

(57) ABSTRACT

A coupling system for receiving a push rod includes a housing defining an internal channel having a sloped wall, and a piston received within the internal channel. The piston includes at least one flexible member arranged within the channel to be acted upon by the sloped wall to engage the push rod. The only external force required to couple the push rod is an axial force on the piston in a direction. The only external force required to de-couple the push rod is an axial force on the piston in an opposite direction.

27 Claims, 14 Drawing Sheets

(56) References Cited

U.S. PATENT DOCUMENTS

| | | | |
|---|---|---|---|
| 3,918,485 A | | 11/1975 | Weber et al. |
| 3,993,061 A | * | 11/1976 | O'Leary .................... 604/152 |
| 4,373,753 A | | 2/1983 | Ayers et al. |
| 4,515,591 A | * | 5/1985 | Hemmerich et al. ........ 604/152 |
| 4,519,792 A | * | 5/1985 | Dawe ........................ 604/152 |
| 4,557,725 A | * | 12/1985 | Heyne et al. ................. 604/67 |
| 4,605,396 A | * | 8/1986 | Tseo et al. .................... 604/32 |
| 4,610,468 A | | 9/1986 | Wood |
| 4,635,621 A | * | 1/1987 | Atkinson .................... 601/161 |
| 4,776,769 A | | 10/1988 | Hilaris |
| 4,778,347 A | | 10/1988 | Mize |
| 4,784,588 A | | 11/1988 | Miyashita et al. |
| 4,792,096 A | | 12/1988 | Gregory |
| 4,798,589 A | * | 1/1989 | Tseo .......................... 604/152 |
| 4,883,409 A | | 11/1989 | Strohmeier et al. |
| 4,902,045 A | | 2/1990 | McGugan et al. |
| 5,011,468 A | | 4/1991 | Lundquist et al. |
| 5,088,898 A | | 2/1992 | Fukumoto et al. |
| 5,127,807 A | | 7/1992 | Eslinger |
| 5,171,045 A | | 12/1992 | Pasbrig |
| 5,259,842 A | | 11/1993 | Plechinger et al. |
| 5,318,518 A | | 6/1994 | Plechinger et al. |
| 5,370,609 A | | 12/1994 | Drasler et al. |
| 5,411,380 A | | 5/1995 | Bristol et al. |
| 5,507,219 A | | 4/1996 | Stogner |
| 5,527,330 A | | 6/1996 | Tovey |
| 5,636,975 A | | 6/1997 | Tiffany et al. |
| 5,788,465 A | | 8/1998 | Luongo et al. |
| 5,853,384 A | | 12/1998 | Bair |
| 5,915,927 A | | 6/1999 | Kuromitsu |
| 5,944,686 A | | 8/1999 | Patterson et al. |
| 6,089,620 A | | 7/2000 | Mota et al. |
| 6,099,502 A | | 8/2000 | Duchon et al. |
| 6,164,188 A | | 12/2000 | Miser |
| 6,216,573 B1 | * | 4/2001 | Moutafis et al. ............... 83/177 |
| 6,224,378 B1 | | 5/2001 | Valdes et al. |
| 6,258,061 B1 | | 7/2001 | Drasler et al. |
| 6,471,683 B2 | | 10/2002 | Drasler et al. |
| 6,497,572 B2 | | 12/2002 | Hood et al. |
| 6,544,209 B1 | | 4/2003 | Drasler et al. |
| 6,689,101 B2 | | 2/2004 | Hjertman et al. |
| 6,719,718 B2 | | 4/2004 | Bonnette et al. |
| 6,773,240 B2 | | 8/2004 | Dong |
| 7,100,846 B2 | | 9/2006 | Pein |
| 7,104,276 B2 | | 9/2006 | Einhaus |
| 7,168,361 B1 | | 1/2007 | Blume |
| 7,431,711 B2 | | 10/2008 | Moutafis et al. |
| 7,553,318 B2 | | 6/2009 | Ammann |
| D611,961 S | | 3/2010 | Boussu et al. |
| 7,717,685 B2 | * | 5/2010 | Moutafis et al. .............. 417/547 |
| 8,337,175 B2 | * | 12/2012 | Dion et al. .................... 417/415 |
| 2002/0176788 A1 | | 11/2002 | Moutafis et al. |
| 2003/0125660 A1 | | 7/2003 | Moutafis et al. |
| 2003/0129068 A1 | | 7/2003 | Oehman |
| 2004/0234380 A1 | * | 11/2004 | Moutafis et al. .............. 417/53 |
| 2006/0100569 A1 | | 5/2006 | McRury et al. |
| 2006/0149193 A1 | | 7/2006 | Hall |
| 2006/0177326 A1 | | 8/2006 | Harada et al. |
| 2006/0264808 A1 | | 11/2006 | Staid et al. |
| 2007/0276421 A1 | | 11/2007 | Pein |
| 2008/0191549 A1 | | 8/2008 | Giering et al. |
| 2009/0043320 A1 | | 2/2009 | Seto et al. |
| 2009/0060764 A1 | | 3/2009 | Mitzlaff et al. |
| 2011/0042413 A1 | | 2/2011 | Nighy et al. |

FOREIGN PATENT DOCUMENTS

| | | |
|---|---|---|
| EP | 319274 B1 | 12/1992 |
| EP | 1565270 B1 | 4/2006 |
| FR | 2812039 A1 | 1/2002 |
| GB | 1412024 A | 10/1975 |
| JP | S56007566 B2 | 1/1981 |
| JP | 2005030365 A | 2/2005 |
| JP | 2006507437 A | 3/2006 |
| WO | WO9421324 A1 | 9/1994 |
| WO | WO2005085639 A1 | 9/2005 |
| WO | WO2008017181 A1 | 2/2008 |
| WO | WO2008084235 A2 | 7/2008 |
| WO | WO2008083278 A3 | 10/2008 |

OTHER PUBLICATIONS

Invitation to Pay Additional fees and, Where Applicable, Protest fees, with Communication relating to the Results of the Partial International Seach, for International Application No. PCT/US2010/061775, mailed Feb. 23, 2011, 4 pages.

International Search Report and Written Opinion for International Application No. PCT/US2010/061775, mailed Jun. 30, 2011.

Patent Examination Report No. 1 for Australian Application No. 2010341458, mailed Dec. 9, 2013.

Notice of Reasons for Rejection in Japanese Application No. 2012-546194, mailed Nov. 4, 2014.

* cited by examiner

DISPOSABLE PUMPING SYSTEM AND COUPLER

CROSS-REFERENCE TO RELATED APPLICATION

The present application is a continuation of U.S. patent application Ser. No. 12/644,391, filed Dec. 22, 2009, titled "Disposable Pumping System and Coupler," now allowed. The contents of the prior application are incorporated herein in their entirety by reference.

BACKGROUND

A high pressure jet of saline can be used to debride traumatic wounds, chronic wounds, and other soft tissue lesions while sparing healthy tissue and promoting the healing process. A wound debridement system includes a console that powers a disposable handset. The handset includes a pump assembly having a fluid feed line, a piston assembly for pressurizing the fluid, and a high pressure outlet hose that delivers the high pressure fluid to a handpiece of the handset. The pump assembly is powered by a reciprocating linear stroke. The console produces up to 600 W of power (0.8 HP) and 2000 lbs. of force, and the pump pressurizes the fluid up to 17,300 psi.

SUMMARY

In one aspect, a coupling system of, for example, a disposable pumping system, for receiving a push rod of, for example, a drive console, includes a housing defining an internal channel having a sloped wall, and a piston received within the internal channel. The piston includes at least one flexible member arranged within the channel to be acted upon by the sloped wall to engage the push rod.

This, and other aspects, may include one or more of the following features. The flexible member is outwardly biased. Multiple flexible members are arranged within the channel. Each of the multiple flexible members is arranged within the channel to be acted upon by the sloped wall to collectively engage the push rod. Each of the multiple flexible members are outwardly biased. The internal channel includes a region within which the piston reciprocates to pump fluid. The internal channel is funnel shaped, having a sloped-wall region and a constant diameter region. Protruding into the internal channel is a restraining member that maintains the piston within the internal channel.

In another aspect, a coupling system for receiving a push rod includes a housing defining an internal channel, and a piston received within the internal channel.

This, and other aspects, may include one or more of the following features. The piston includes at least one member configured to couple and de-couple the push rod. The only external force required to couple the push rod is an axial force on the piston in a first direction. The only external force required to de-couple the push rod is an axial force on the piston in a second direction opposite the first direction.

In another aspect, a method includes axially advancing a coupling system such that a piston of the coupling system contacts a push rod. The piston is received within a channel of the coupling system.

This, and other aspects, may include one or more of the following features. The channel has a sloped wall. The method includes further axially advancing the coupling system such that the sloped wall acts on the at least one flexible member of the piston to deflect the flexible member into engagement with the push rod.

In another aspect, a method includes coupling a piston and a push rod. The only external force required for the coupling is an axial force applied to the piston by the push rod such that the piston moves into engagement with the push rod.

This, and other aspects, may include one or more of the following features. The method includes decoupling the piston and the push rod. The only external force required for the de-coupling is an axial force applied to the piston by the push rod such that the piston disengages the push rod.

In another aspect, a fluid pump includes a housing having an inflow section defining an inflow chamber and an outflow section defining an outflow chamber, an inflow ball valve including a ball located in the inflow chamber, and outflow ball valve including a ball located in the outflow chamber, the housing defining an internal channel in fluid communication with the inflow section and the outflow section, and a piston located within the internal channel. The piston is configured to pump fluid from the inflow section into the channel and from the channel into the outflow section.

This, and other aspects, may include one or more of the following features. A ratio of a diameter of the ball included in the inflow ball valve to a diameter of the inflow chamber is 1:1.088. A ratio of the diameter of the ball included in the inflow ball valve to a piston stroke is 1:2.160. A ratio of a diameter of the internal channel to the ball included in the inflow ball valve is 1:1.786. A ratio of the diameter of the inflow chamber to a diameter of the housing defining the internal channel is equal to or about 1:3.857.

This, and other aspects, may include one or more of the following features. The inflow ball valve and the outflow ball valve have a stroke of about 0.015 inches.

In another aspect, a fluid pump includes a housing defining an internal channel having a sloped wall, first and second fluid flow chambers in the housing in fluid communication with the internal channel, a first ball valve including a ball located in the first fluid chamber, a second ball valve including a ball located in the second fluid chamber, and a piston received in the housing. The piston is configured to be acted upon by the sloped wall to couple to a push rod for movement therewith. Reciprocal movement of the piston causes fluid inflow through the first fluid chamber and fluid outflow through the second fluid chamber.

This, and other aspects, may include one or more of the following features. The piston includes multiple outwardly biased members that are acted upon by the sloped wall. The internal channel is funnel shaped.

In another aspect, a pumping system includes a console having an interface for receiving a fluid pump. The console including a reciprocally driven push rod and the fluid pump has a piston configured to be driven by the push rod. The interface includes a rotatable sleeve and the fluid pump has a mating feature configured to rotate the rotatable sleeve upon the application of a rotary force to the mating feature to lock and unlock the fluid pump to and from the console.

This, and other aspects, may include the console having a magnet for holding the rotatable sleeve in the locked position.

The details of one or more implementations of the specification are set forth in the accompanying drawings and the description below. Other features and aspects of the specification will become apparent from the description, the drawings, and the claims.

DETAILED DESCRIPTION

Figure 1:
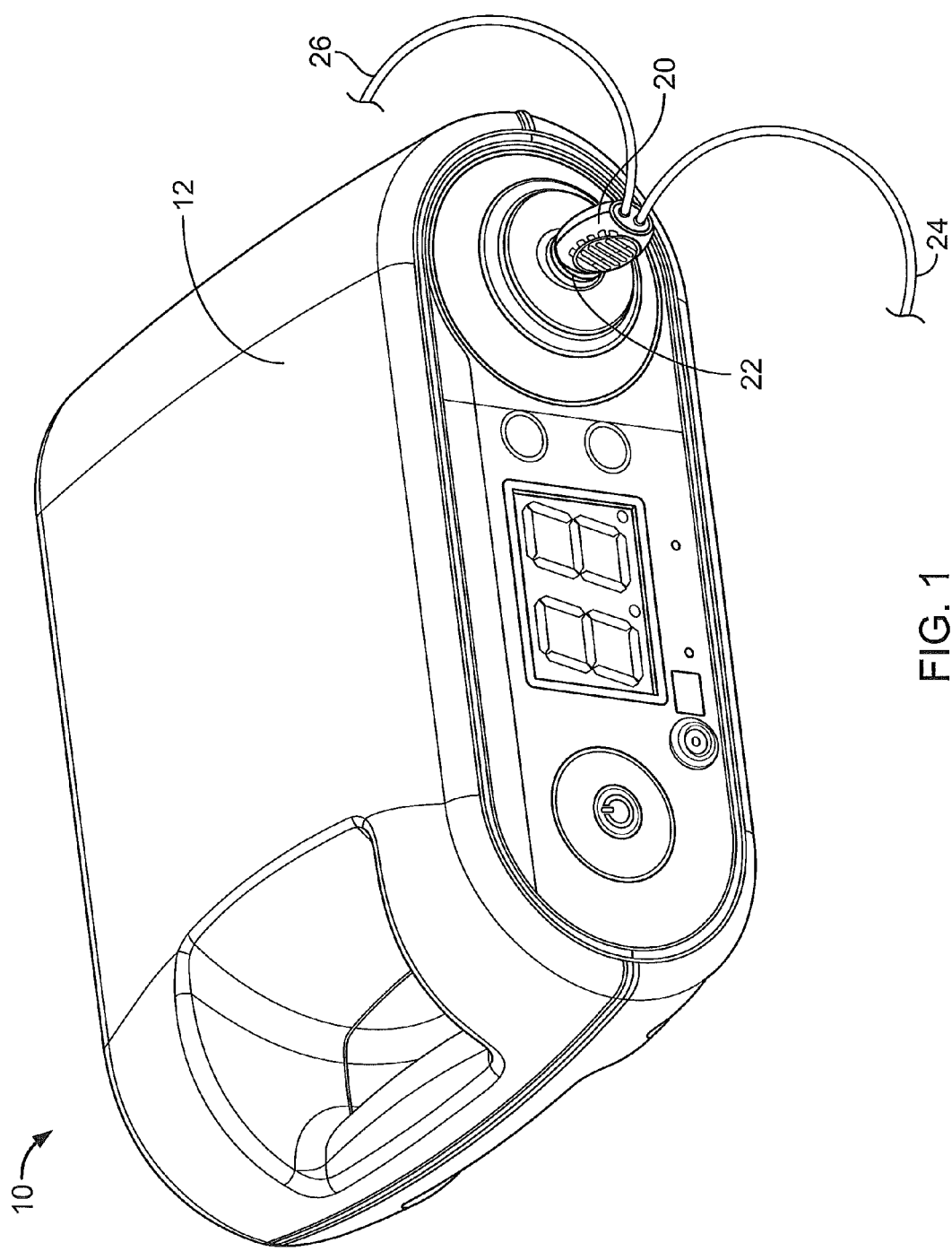
FIG. 1 is a perspective view of a drive console and a pump.
Figure 2:
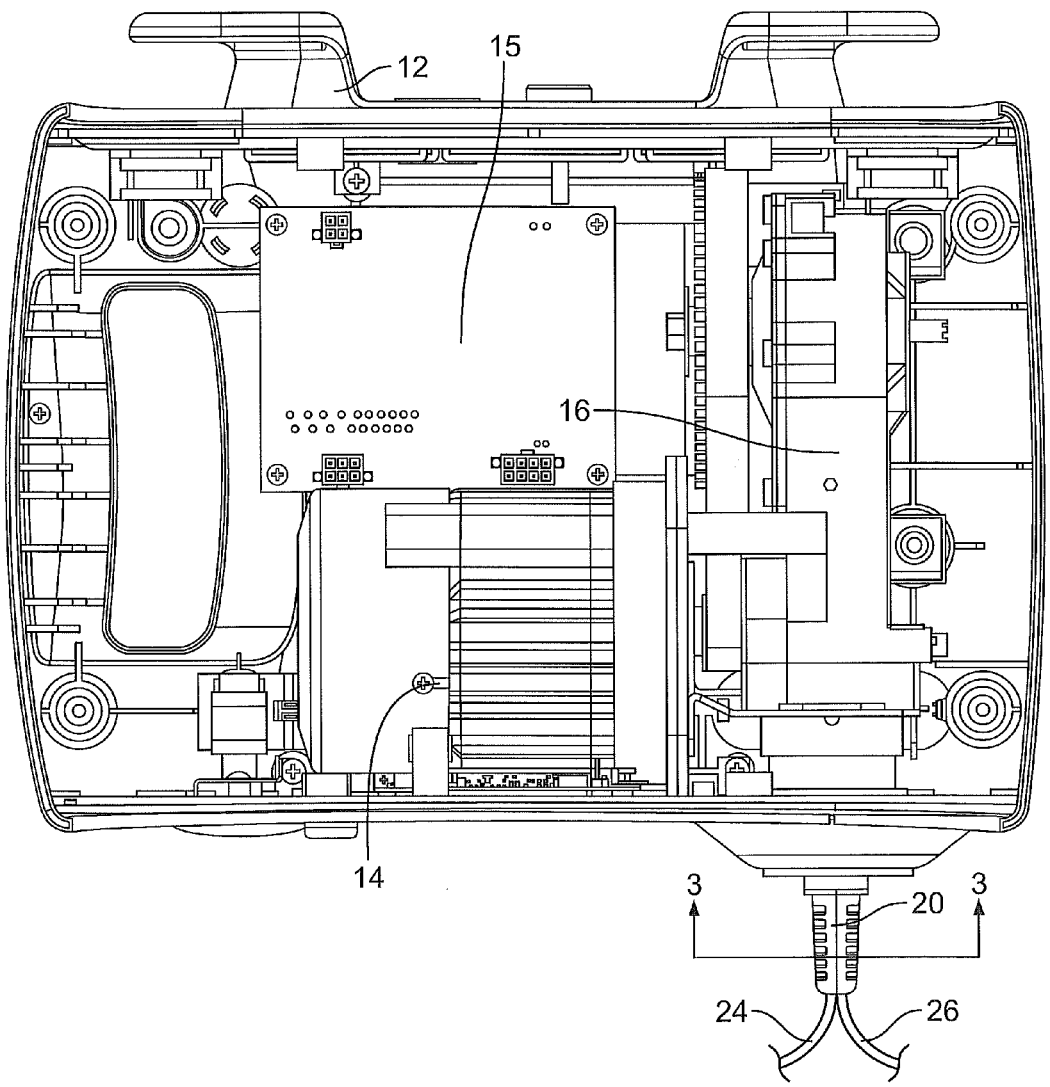
FIG. 2 is a top view of the drive console and pump with the console cover removed.

Referring to FIGS. 1 and 2, a pump system 10 for regulating pumping of a fluid to, for example, a medical instrument such as a wound bed preparation device, includes a drive console 12. The drive console 12 is an electro-mechanical drive train that houses a motor 14, a power board 15 including circuitry, and a transmission 16 for driving a push rod 18 (FIG. 8), as described with reference to U.S. Published application numbers 2003/0125660, 2004/0234380, and 2006/0264808, and WO 2008/083278, all hereby incorporated by reference in their entirety. The pump system 10 includes a disposable pump 20 housing valve pump components, discussed further below. The pump 20 removably mates with an interface 22 of the drive console 12 such that the pump components of the pump 20 are acted upon by the push rod 18 to draw fluid into the pump 20 from an inlet line 24 and to pump pressurized fluid through an outlet line 26 for delivery to the medical instrument.

Figure 3:
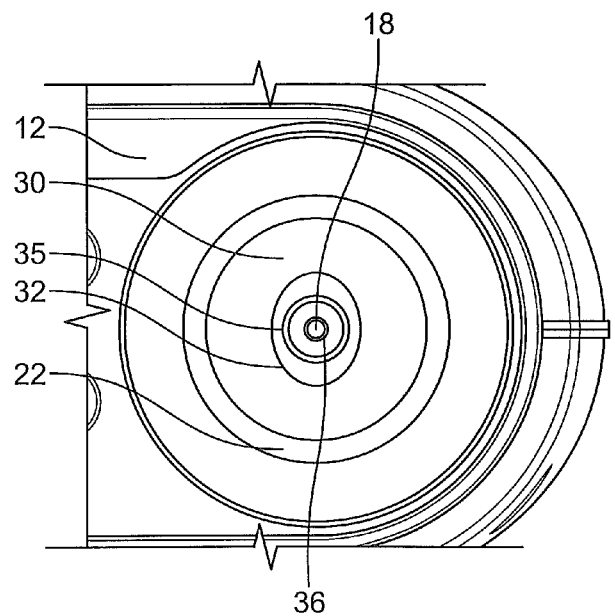
FIG. 3 is an end view of an interface of the drive console taken along lines 3-3 of FIG. 2.
Figure 4:
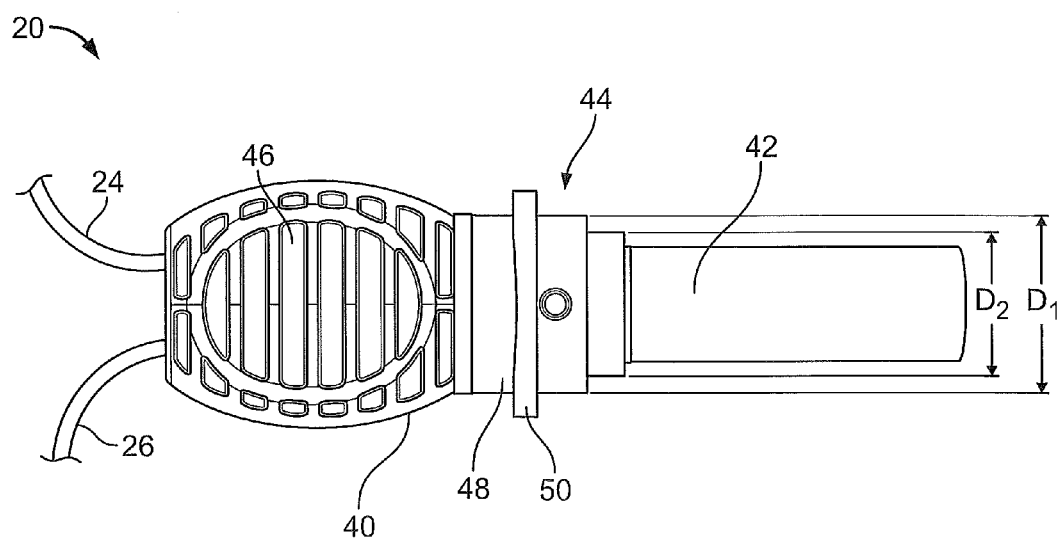
FIG. 4 is a side view of the pump.
Figure 5:
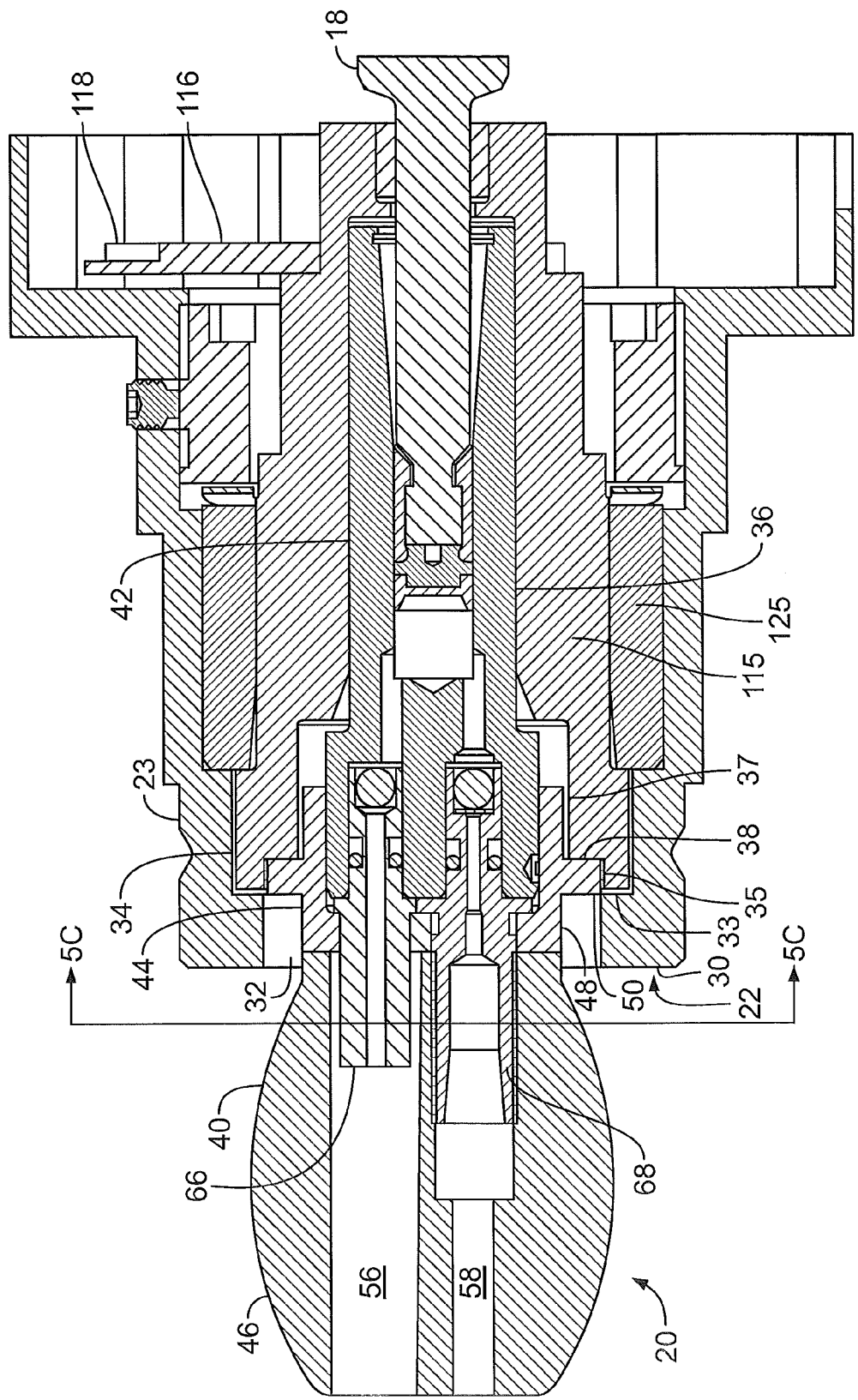
FIG. 5 is a cross-sectional view of the console interface and pump shown in an open position.
Figure 5A:
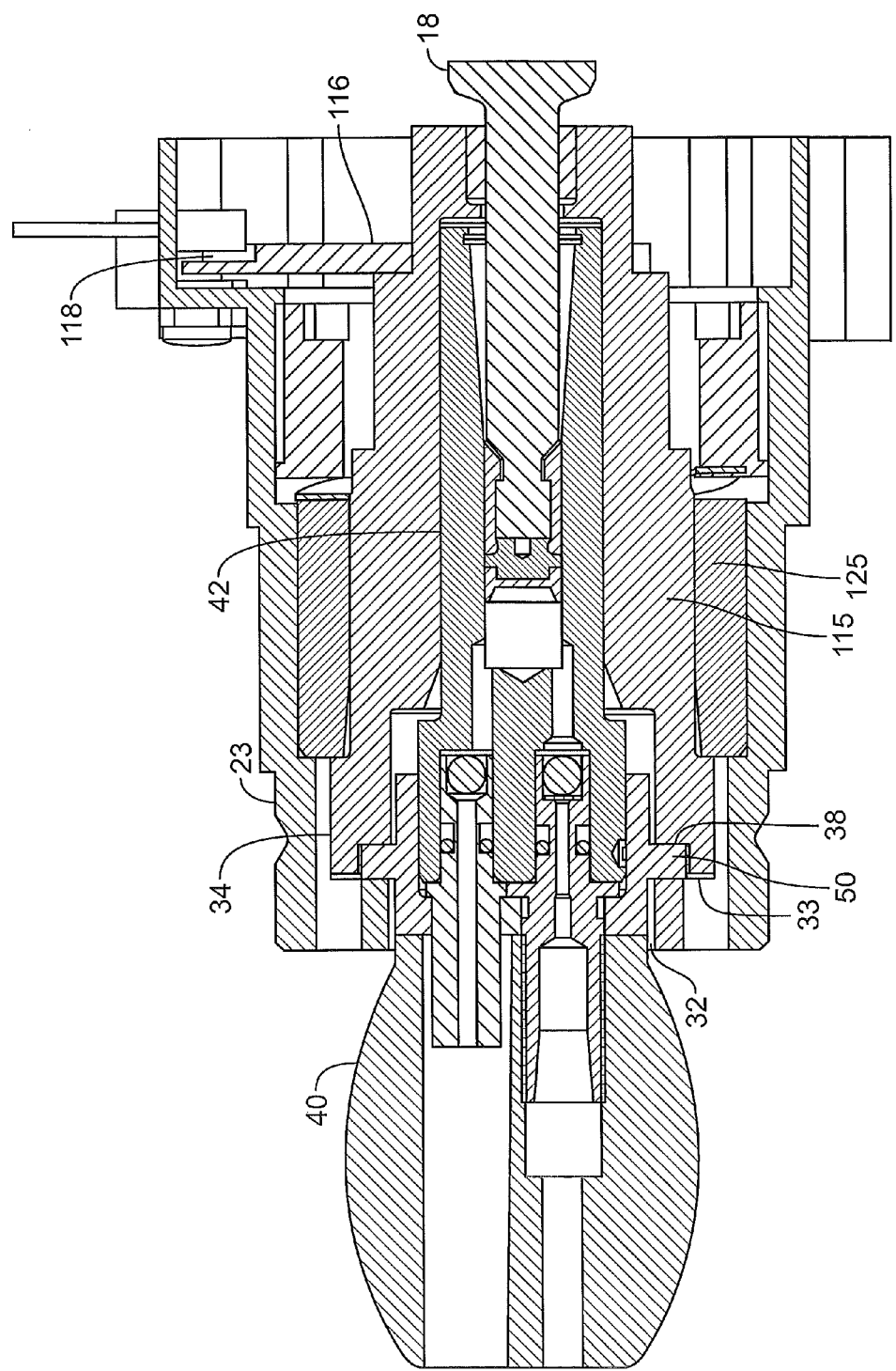
FIG. 5A is a cross-sectional view of the console interface and pump shown in a closed position.
Figure 5B:
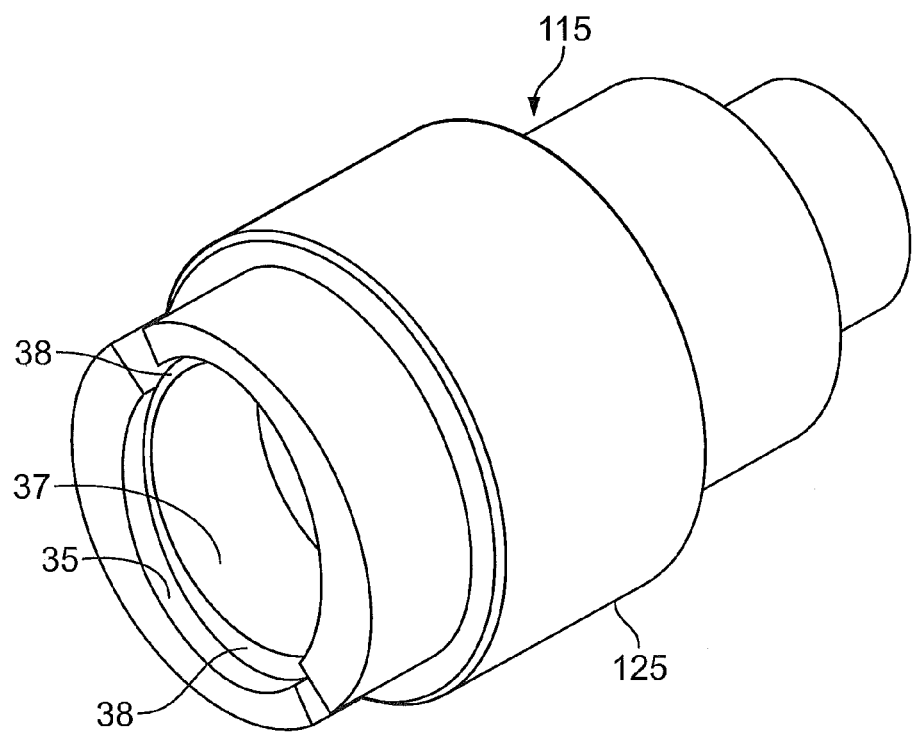
FIG. 5B is a perspective view of a rotatable sleeve of the console interface.
Figure 5C:
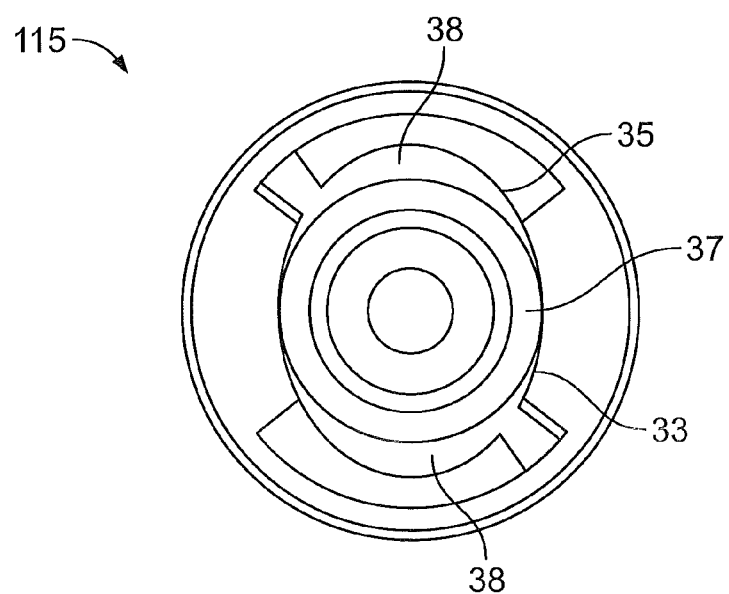
FIG. 5C is an end view of the console interface.

Referring to FIGS. 3-5, the console interface 22 includes a housing 23 having a face 30 through which an outermost, oval bore 32 extends. Behind the oval bore 32, the housing 23 includes a cylindrical bore 34 having a diameter larger than the larger diameter of the oval bore 32, such that a shelf 33 is formed at the intersection of the bores 32 and 34. The cylindrical bore 34 receives a sleeve 115 that is rotatable relative to the housing 23 and includes a bearing 125 for this purpose. The sleeve 115 defines an oval bore 35 and a cylindrical bore 37 of smaller diameter than the larger diameter of the oval bore 35 such that a shelf 38 is formed at the intersection of the bores 35 and 37 (FIGS. 5B and 5C). The sleeve 115 defines an additional cylindrical bore 36.

The pump 20 has a pump housing 40 with a cylindrical insert section 42, a central coupling section 44, and a handle 46. The insert section 42 is received within the bore 36 of the housing 23, and the coupling section 44 is received within the bores 32, 35, and 37 to lock the pump 20 to the console 12. The coupling section 44 includes a cylindrical portion 48 of greater diameter, D1, than diameter D2 of coupling insert section 42. Extending outward from portion 48 is a mating feature, for example, an oval flange 50, dimensioned to be received within oval bore 35 of the console interface 22 in a close fit.

Figure 13A:
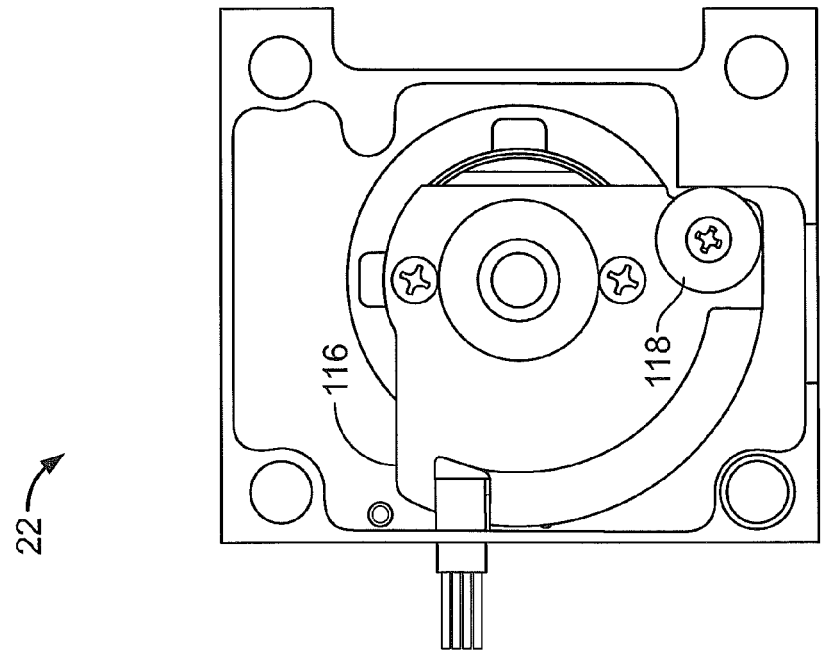
FIGS. 13 and 13A illustrate a locking feature of the console interface shown in the open position in FIG. 13 and in the locked position in FIG. 13A.
Figure 13:
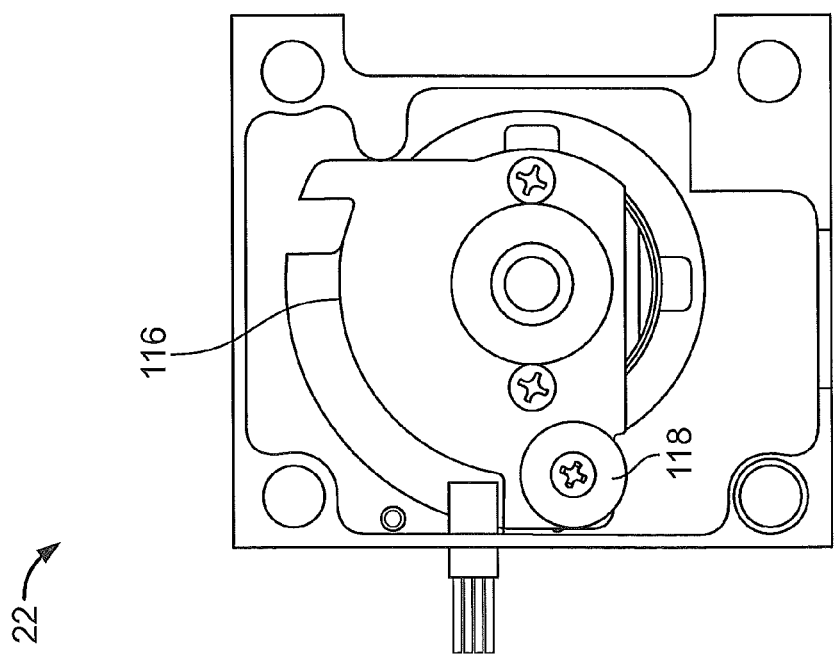

To securely attach the pump 20 to the drive console 12, the operator inserts the cylindrical insert section 42 through the oval bore 32 into the bore 36 with the oval flange 50 of the pump 20 aligned to be received through the oval bore 32 of the housing 23 and into the oval bore 35 of the sleeve 115. When the pump is inserted to where the pump flange 50 abuts the console interface shelf 38, the operator rotates the pump handle 46 90 degrees such that the flange 50 is locked between the shelves 33 and 38 (FIG. 5A). The sleeve 115 rotates with the pump 20, thereby locking the flange 50 between the shelves 33 and 38. To release the pump 20 from the drive console 12, the operator rotates the handle 46 in the opposite direction to align the pump flange 50 and the bore 32, and pulls the pump from the console. Attached to the backside of the sleeve 115 of the console interface 22 is a plate 116 that includes a magnet 118 (FIG. 13) for holding the rotatable sleeve 115 in the locked position.

Figure 6:
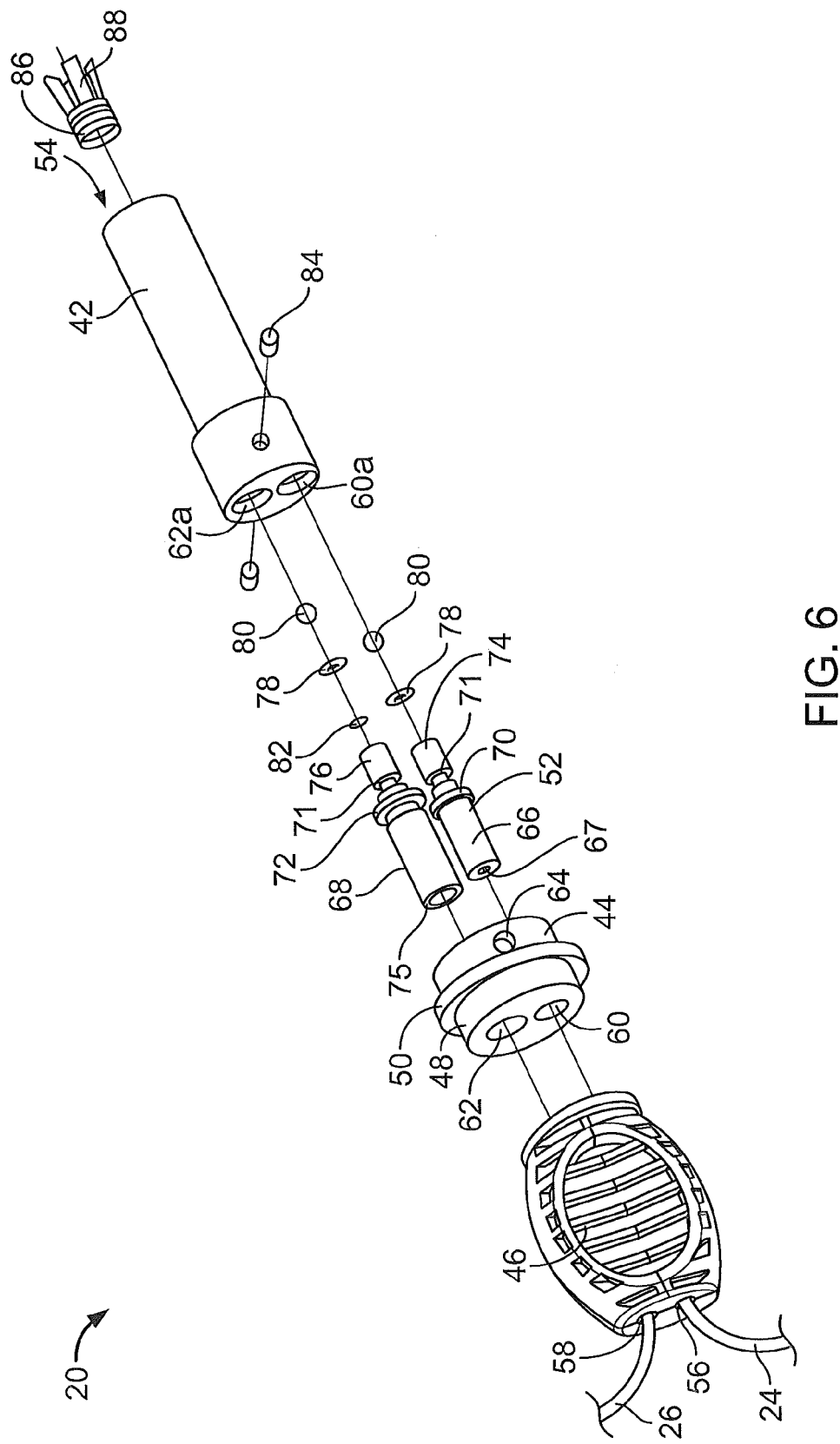
FIG. 6 is an exploded view of the pump.

Referring to FIGS. 5 and 6, the pump 20 includes a ball valve assembly 52 received within the central coupling section 44 and the cylindrical insert section 42, and a push rod-piston coupling system 54 received within the cylindrical insert section 42. The ball valve assembly 52 includes an inflow member 66 defining an inlet passage 67 and an inlet valve chamber 69. Housed within the inlet valve chamber 69 is a ball 80, and located within a groove 71 on the outer surface of the inflow member 66 is an o-ring seal 78. At the intersection of the inlet passage 67 and the inlet valve chamber 69, a valve seat 70 is formed. The ball valve assembly 52 also includes an outflow member 68 defining an outlet valve chamber 73 and an outlet passage 75. Housed within the outlet valve chamber 73 is a ball 80, and located within a groove 71 on the outer surface of the outflow member 69 is an o-ring seal 78. Also located within outlet valve chamber 73 is a screen 82 and a screen retainer 82a.

The central coupling section 44 defines bores 60, 62 that receive members 66, 68, respectively, and the cylindrical insert section 42 defines bores 60a, 62a that receive members 66, 68, respectively. The cylindrical insert section 42 is received within a counterbore 77 in central coupling section 44 and secured thereto with pins 84. The pump handle 46 defines a bore 56 in fluid communication with inlet passage 67, and a bore 58 in fluid communication with outlet passage 75. The inlet line 24 and outlet line 26 are received within the bores 56, 58, respectively.

The cylindrical insert section 42 further defines inflow and outflow passages 85, 87 and a fluid chamber 89. At the intersection of the outflow passage 87 and the outlet valve chamber 73, a valve seat 72 is formed. As described further below, in operation, fluid is pumped through the inlet line 24 into the inlet passage 67 and valve chamber 69, through inflow passage 85 and into fluid chamber 89; and the fluid is pumped out through outflow passage 87, into valve chamber 73 and outlet passage 75 into outlet line 26.

Figure 7:
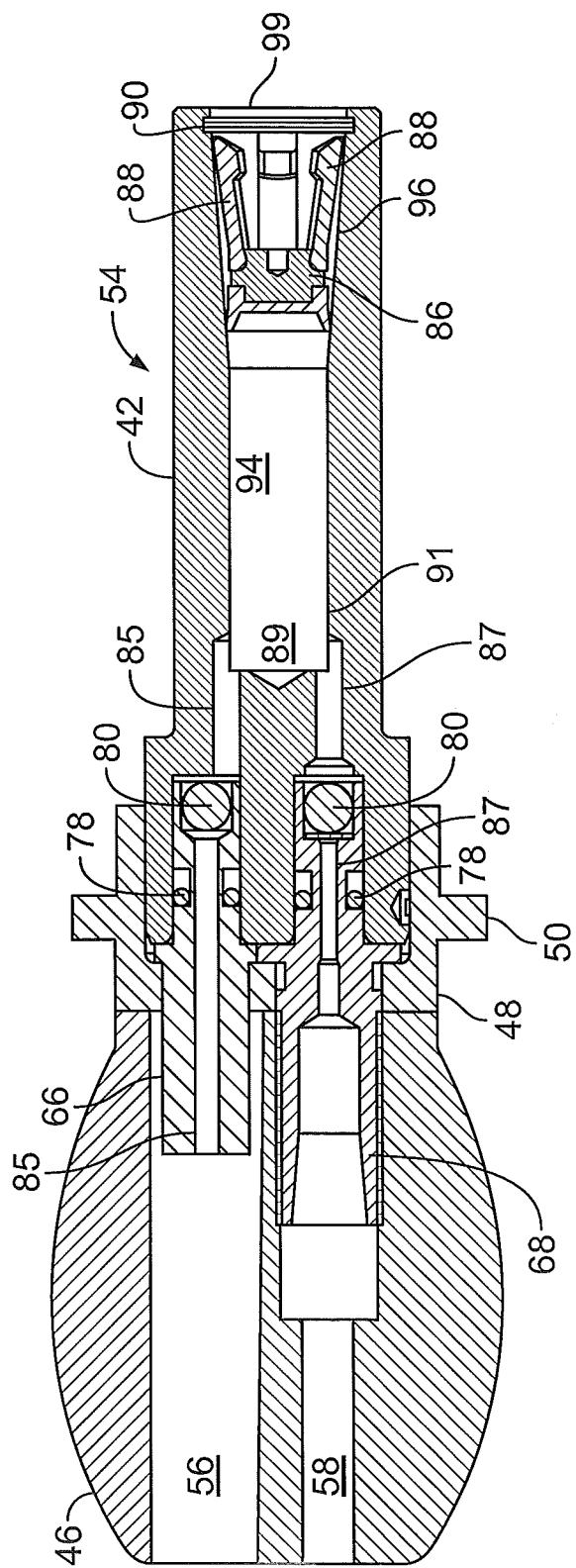
FIG. 7 is a cross-sectional view of the pump.

Referring also to FIG. 7, the push rod-piston coupling system 54 includes an internal channel 94 defined within the cylindrical insert 42. The internal channel 94 has a cylindrical bore section 91 that forms the fluid chamber 89, and a section 96 having outwardly sloped walls such that the internal channel 94 is funnel shaped. The internal channel 94 has an open end 99 for receiving the push rod 18. Slidably received within sections 91 and 96 is a piston 86 including four flexible members 88 that connect to the push rod 18 of the drive console, as described below. Also located within the section 96 is a restraining member 90, for example, a snap ring, that protrudes into channel 94 to keep the piston from sliding out of the insert section 42.

Figure 8:
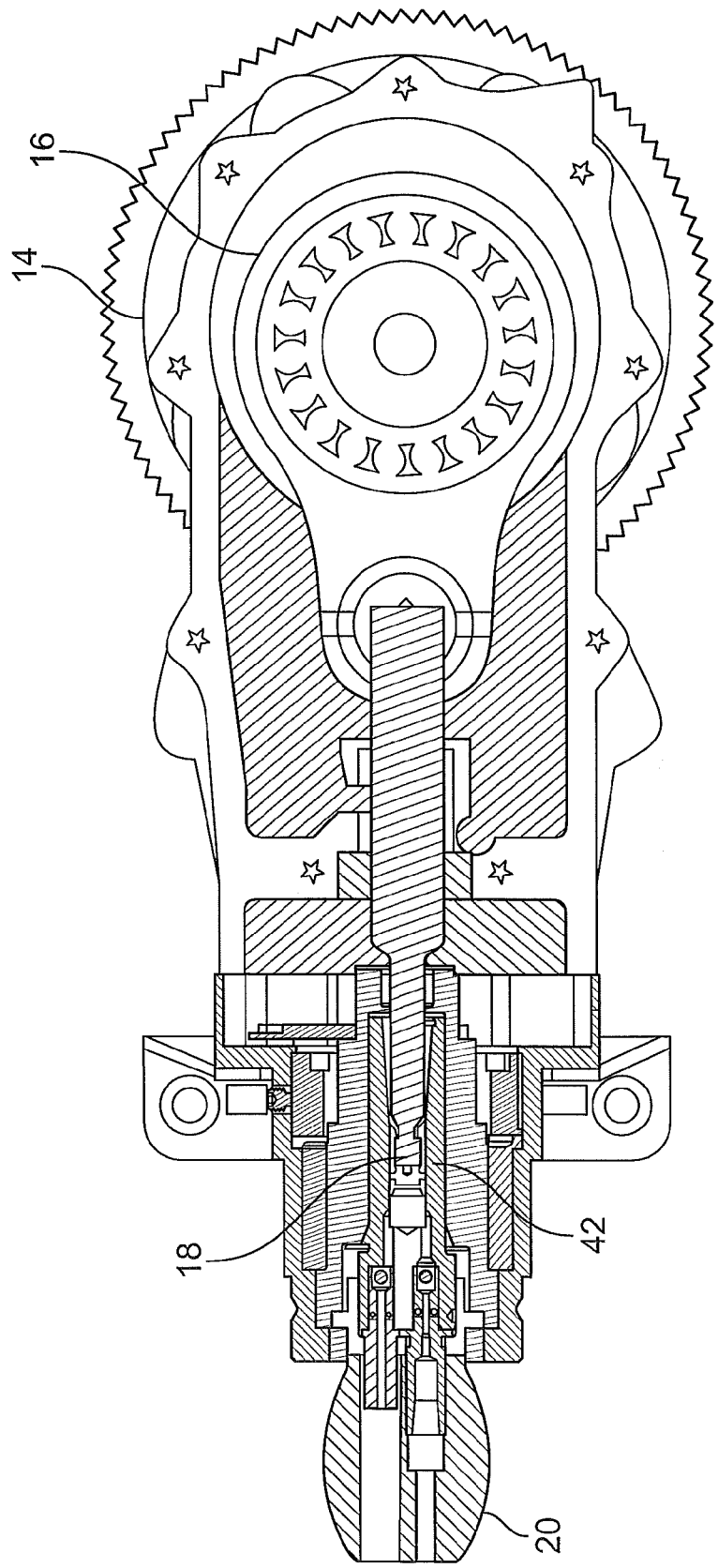
FIG. 8 is a cross-sectional view of a portion of the drive console including a push rod and of the pump.
Figure 9:
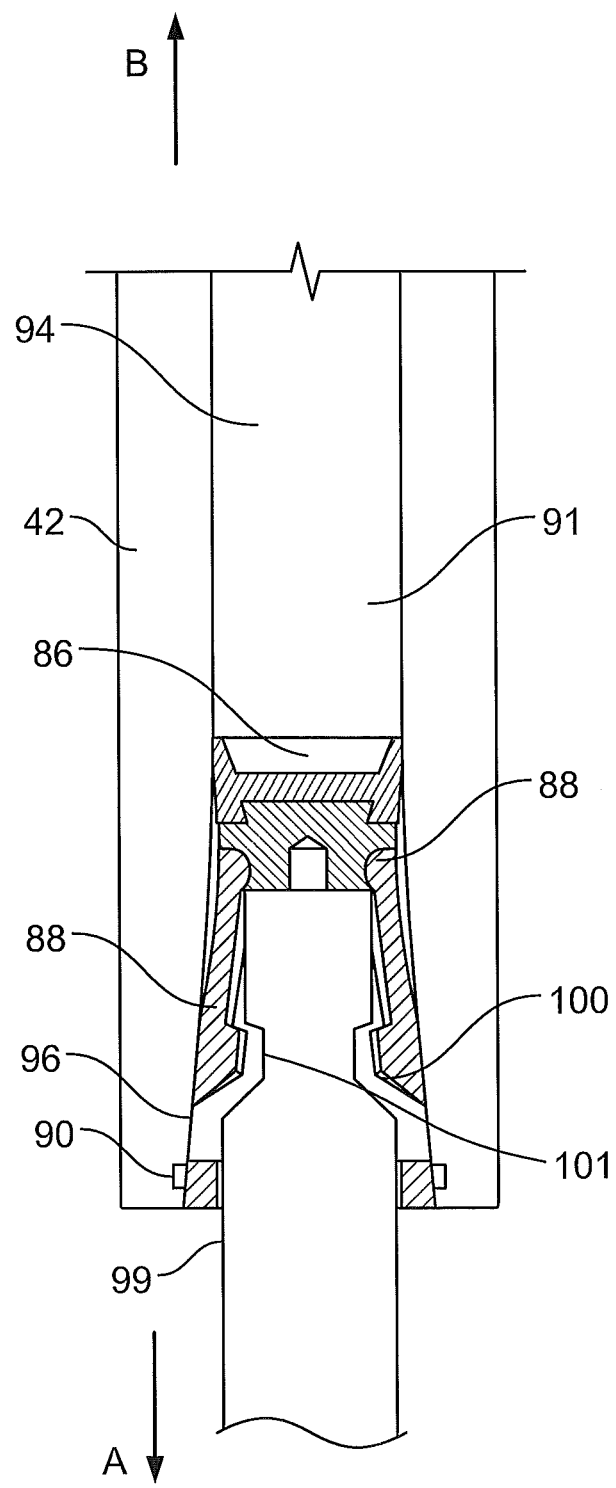
FIGS. 9-11 show the coupling of a piston of the pump with the push rod of the drive console.
Figure 10:
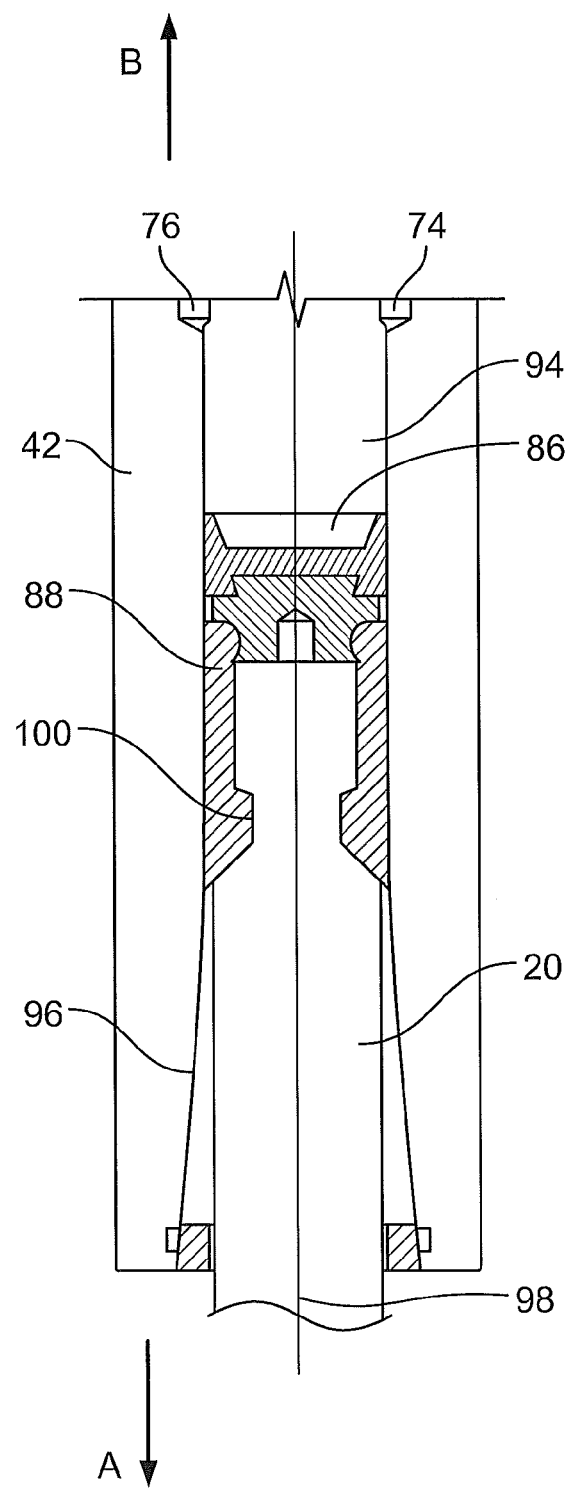

As illustrated in FIG. 8, in operation the piston 86 couples the pump 20 to the push rod 18. The motor 14 and the transmission 16 cause reciprocating motion of the push rod 18, which in turns causes the piston 86 to reciprocate and pump fluid into and out of the pump chamber 89. Referring to FIG. 9, the flexible members 88 of the piston 86 are outwardly biased and connect to and disconnect from the push rod 18 simply by the action of inserting the pump 20 into the drive console and removing the pump 20 from the drive console as described above. When the pump 20 is inserted into the drive console, the push rod 18 enters the sloped wall section 96 through the open end 99, and the piston 86 initially engages the push rod 18. Further advancement of the pump, arrow A, results in the push rod 18 pushing the piston 86 down the sloped wall section 96 in the direction of arrow B, opposite arrow A, toward the section 91. The sloped wall section 96 acts to compress the flexible members 88 until hook members 100 of the flexible members 88 are received within a groove 101 of the push rod 18 to couple the piston 86 to the push rod 18 (FIG. 10). Thus, the only external force required to couple the push rod 18 and the piston 86 is an axial force on the piston 86 applied in the direction of arrow B by the push rod 18. In this manner, the piston 86 initially engages the push rod 18 when axially advanced into contact with the push rod 18, and couples with the push rod 18 when the pump 20 is further axially advanced. Once the pump 20 is locked in position, the reciprocating motion of the piston 86 occurs between the positions illustrated in FIGS. 10 and 11.

To de-couple the push rod 18 and the piston 86, the pump 20 is withdrawn from the drive console, as described above. The axial withdrawal of the pump 20 in the direction of arrow B results in the piston 86 traveling in the direction of arrow A toward the sloped wall section 96. When the flexible members 88 enter the sloped wall section 96, the flexible members 88 flex outward due to their outward bias, releasing the push rod 18 such that the pump 20 can be fully removed. Thus, the only external force required to de-couple the push rod 18 and the piston 86 is an axial force on the piston 86 in the direction of arrow A applied by the push rod 18.

Figure 11:
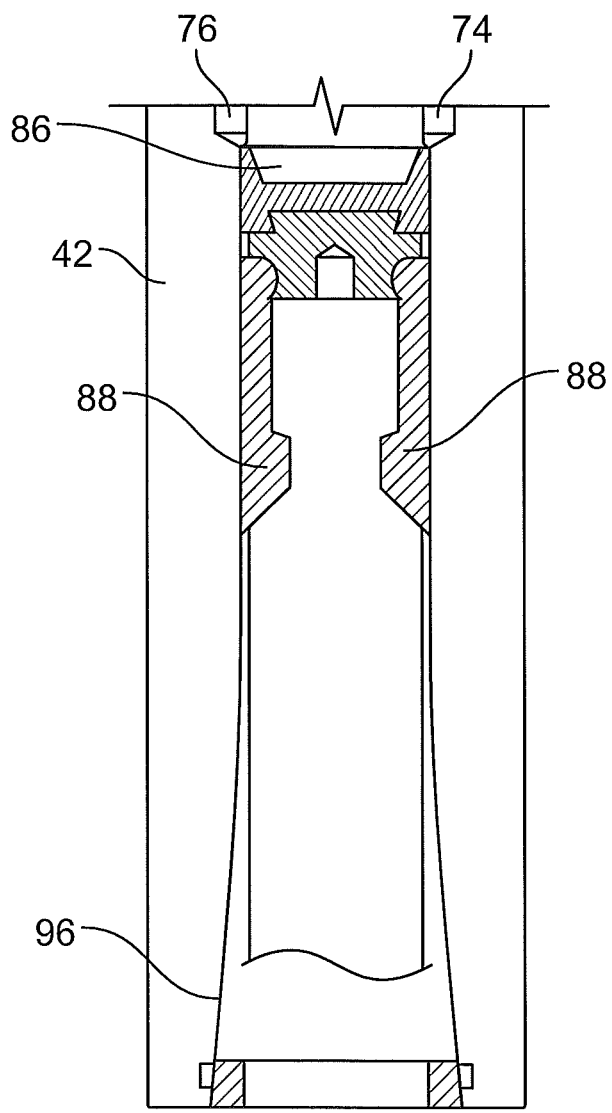

In operation, when the push rod 18 and the piston 86 are coupled, moving the piston from the position shown in FIG. 11 to the position shown in FIG. 10 pulls fluid into fluid chamber 89 from the inlet line 24, and moving the piston 86 from the position shown in FIG. 11 to the position shown in FIG. 10 pushes pressurized fluid out of fluid chamber 89 and to the outlet line 26. The reciprocal motion imparted by the push rod 18 to the piston 86 acts to continuously pump fluid.

Figure 12:
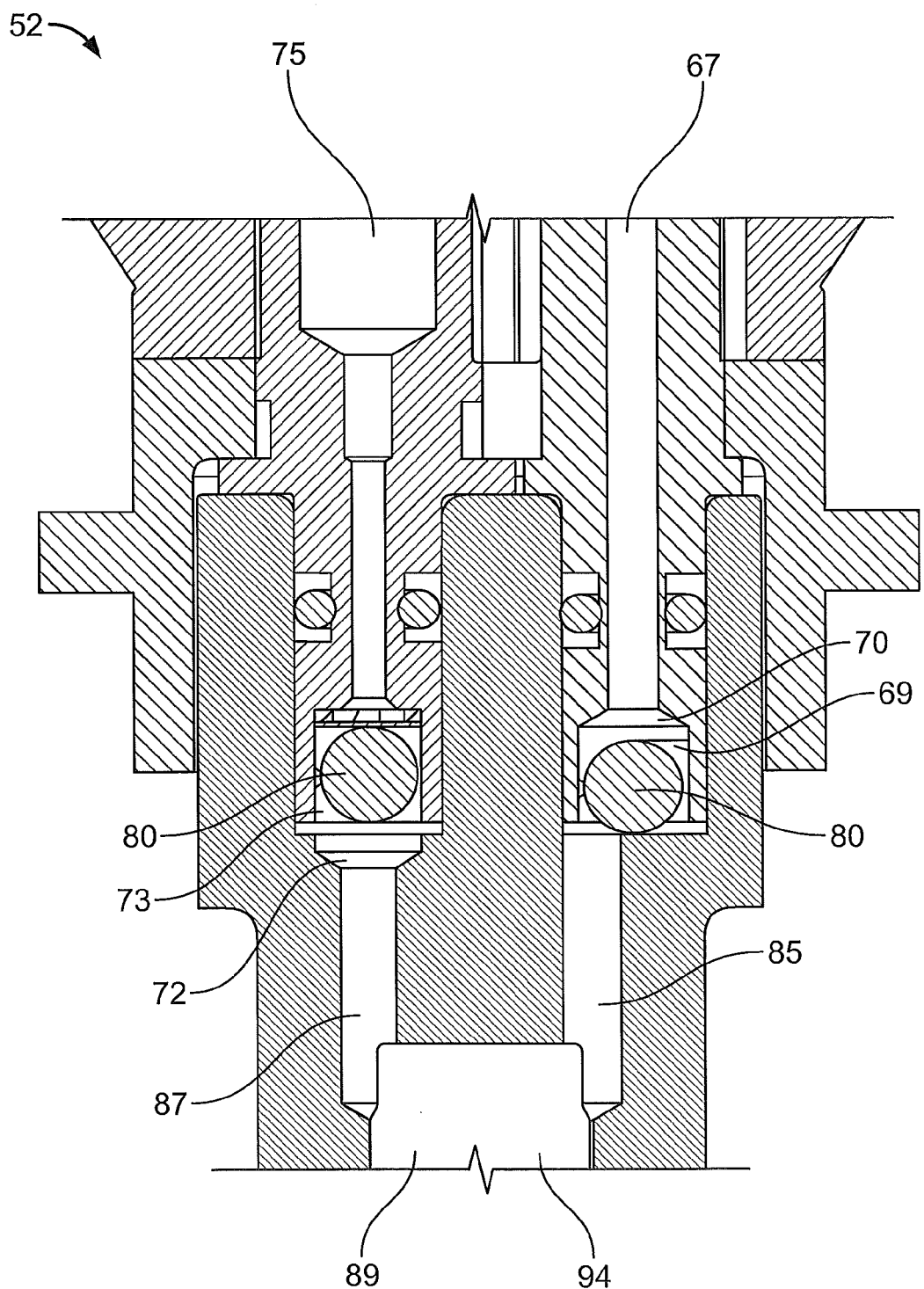
FIG. 12 is a cross-sectional view of pumping components housed within the pump.

Referring to FIG. 12, when the periodic motion of the push rod 18 causes the piston 86 to move from top dead center (FIG. 11) to bottom dead center (FIG. 12), the inflow chamber ball 80 is pulled away from the valve seat 70, such that fluid is suctioned from the inlet line 24 into the cavity 89, and the outflow ball 80 is pulled into engagement with valve seat 72. When the piston 86 moves in the opposite direction, the inflow chamber ball 80 is pushed into engagement with the inflow chamber valve seat 70, and the outflow ball 80 is pushed away from the valve seat 72 to permit fluid outflow through outlet line 26.

The pressure of the fluid entering in the pump 20 can be, for example, atmospheric pressure to 2 psi above atmosphere, depending on the height of a fluid supply bag relative to the console. Depending on user controlled settings, the fluid pressure produced by the pump and delivered through the nozzle of an attached handpiece, is the range of, for example, 1,882 to 15,214 psi.

The components of the ball valve assembly 52 are selected to obtain precise flow rates and fluid pressures. For example, the diameter of each of the inflow chamber and outflow chamber balls 80 is 0.125"±0.0011". Each of the balls 80 is a wear-resistant stainless steel ball weighing 0.0046 oz. The inflow chamber 66 and the outflow chamber 68, each have a cylindrical cross-section of diameter 0.063"±0.003". The inflow valve stroke and the outflow valve stroke are each 0.015". The inflow valve seat angle and the outflow valve seat angle are each 118°±2°. A ratio of the ball diameter to chamber diameter is 1:1.088. A ratio of the ball diameter to piston stroke is 1:2.160. A ratio of the inflow chamber diameter and the cavity in the internal channel 94 is 1:2.19. A ratio of the channel diameter to ball diameter is 1:1.1786, and a ratio of the inflow chamber diameter to bore diameter is 1:3.857. The cylindrical insert 42 in which the internal channel 94 is defined is 1.2" long, of which the region having the sloped wall 96 is 0.45" long. The angle of the slope is 8°. The end of the cylindrical insert 42 that is attached to the inflow section 74 and the outflow section 76 has a 90° taper in the internal channel 806, that has a larger diameter of 0.312". The outer diameter of the housing 804 is 0.358"±0.002". A fluid pump of these dimensions operates in a pressure range between 0-18,000 psi and pumps fluids in a flow rate range of 0-400 ml/min.

Other embodiments are within the scope of the following claims. For example, rather than the cross-sectional shapes of the pump 20 and the drive console 12 being cylindrical and oval, the cross-sectional shapes can be square, rectangle, or combinations of all of these shapes. Rather than the piston 86 including four flexible members 88, the piston can have one, two, three or more flexible members.

What is claimed is:

1. A pump system, comprising:
a pump console housing a push rod, a motor and a transmission for driving the push rod in an axially reciprocal motion, the console including a pump interface;
a disposable pump configured to removably mate with the pump interface by advancing the disposable pump in an axial direction corresponding to the axis of reciprocal motion of the push rod such that the push rod extends into an internal channel of the disposable pump, the disposable pump including a housing having an inflow section defining an inflow chamber, and an outflow section defining an outflow chamber, the inflow section and the outflow section being located side-by-side in the housing, an inflow valve located in the inflow chamber and an outflow valve located in the outflow chamber, the housing defining the internal channel, the internal channel axially aligned with and in fluid communication with the inflow section and the outflow section, and a piston located within the internal channel and configured to mate with the push rod for axial reciprocal movement therewith within the internal channel to pump fluid from the inflow section into the internal channel and from the internal channel into the outflow section;
a fluid inlet line to the inflow section of the disposable pump; and
a fluid outlet line from the outflow section of the disposable pump.

2. The pump system of claim 1 wherein the internal channel has a sloped wall.

3. The pump system of claim 2 wherein the piston includes at least one flexible member arranged within the internal channel to be acted upon by the sloped wall to engage the push rod.

4. The pump system of claim 3 wherein the internal channel includes a region within which the piston is configured to reciprocate while the flexible member is engaged with the push rod.

5. The pump system of claim 3 wherein the flexible member is outwardly biased.

6. The pump system of claim 3 wherein a plurality of flexible members are arranged within the internal channel, each of which is arranged within the internal channel to be acted upon by the sloped wall to collectively engage the push rod.

7. The pump system of claim 6 wherein each of the plurality of flexible members is outwardly biased.

8. The pump system of claim 1 wherein the internal channel is funnel shaped.

9. The pump system of claim 1 further comprising a restraining member protruding into the internal channel to maintain the piston within the internal channel.

10. The pump system of claim 1 wherein the piston includes at least one flexible member configured to couple and de-couple the push rod, wherein the only external force required to couple the push rod is an axial force on the piston in a first direction, and the only external force required to de-couple the push rod is an axial force on the piston in a second direction opposite the first direction.

11. The pump system of claim 1 wherein the inflow valve comprises an inflow ball valve and the outflow valve comprises an outflow ball valve.

12. The pump system of claim 11 wherein the inflow ball valve and the outflow ball valve have a stroke of about 0.015 inches.

13. The pump system of claim 1 wherein the pump interface includes a rotatable sleeve and the disposable pump includes a mating feature configured to rotate the rotatable sleeve upon the application of a rotary force to the mating feature to lock and unlock the disposable pump to and from the pump console.

14. The pump system of claim 13 wherein the pump console includes a magnet for holding the rotatable sleeve in the locked position.

15. A method, comprising:
mating a disposable pump with a pump interface of a pump console;
delivering fluid to an inflow chamber of an inflow section of the disposable pump through a fluid inlet line of the disposable pump;
moving an inflow valve located in the inflow chamber to deliver fluid from the inflow chamber to an internal channel of the disposable pump; and
moving an outflow valve locating in an outflow chamber of an outflow section of the disposable pump to deliver fluid from the internal channel to the outflow chamber, the inflow section and the outflow section being located side-by-side and the internal channel being axially aligned with the inflow section and the outflow section;
wherein moving the inflow valve and the outflow valve comprises driving a push rod of the pump console in an axially reciprocal motion to move a piston of the disposable pump, the push rod extending into the internal channel and the piston located within the internal channel and mated with the push rod for axial reciprocal movement therewith within the internal channel; and
wherein mating the disposable pump with the pump interface comprises advancing the disposable pump in an axial direction corresponding to the axis of reciprocal motion of the push rod.

16. The method of claim 15 wherein advancing the disposable pump causes a sloped wall of the internal channel to act on at least one flexible member of the piston to deflect the at least one flexible member into engagement with the push rod.

17. The method of claim 15 further comprising moving the piston into engagement with the push rod by the application of an axial force applied to the piston by the push rod.

18. The method of claim 15 further comprising disengaging the piston from the push rod by the application of an axial force applied to the piston by the push rod.

19. The method of claim 15 further comprising applying a rotary force to lock and unlock the disposable pump to and from the pump console.

20. A pump system, comprising:
a pump console housing a push rod, a motor and a transmission for driving the push rod in an axially reciprocal motion, the console including a pump interface;
a disposable pump configured to removably mate with the pump interface by advancing the disposable pump in an axial direction corresponding to the axis of reciprocal motion of the push rod, the disposable pump including a housing having an inflow section defining an inflow chamber, and an outflow section defining an outflow chamber, the inflow section and the outflow section being located side-by-side in the housing, an inflow valve located in the inflow chamber and an outflow valve located in the outflow chamber, the housing defining an internal channel axially aligned with and in fluid communication with the inflow section and the outflow section, the internal channel having a sloped wall, and a piston located within the internal channel and configured to mate with the push rod for axial reciprocal movement therewith to pump fluid from the inflow section into the internal channel and from the internal channel into the outflow section, the piston including a plurality of flexible members arranged within the internal channel, each of which is arranged within the internal channel to be acted upon by the sloped wall to collectively engage the push rod;
a fluid inlet line to the inflow section of the disposable pump; and
a fluid outlet line from the outflow section of the disposable pump.

21. The pump system of claim 20 wherein each of the plurality of flexible members is outwardly biased.

22. A pump system, comprising:
a pump console housing a push rod, a motor and a transmission for driving the push rod in an axially reciprocal motion, the console including a pump interface;
a disposable pump configured to removably mate with the pump interface by advancing the disposable pump in an axial direction corresponding to the axis of reciprocal motion of the push rod, the disposable pump including a housing having an inflow section defining an inflow chamber, and an outflow section defining an outflow chamber, the inflow section and the outflow section being located side-by-side in the housing, an inflow valve located in the inflow chamber and an outflow valve located in the outflow chamber, the housing defining an internal channel axially aligned with and in fluid communication with the inflow section and the outflow section, and a piston located within the internal channel and configured to mate with the push rod for axial reciprocal movement therewith to pump fluid from the inflow section into the internal channel and from the internal channel into the outflow section;

a fluid inlet line to the inflow section of the disposable pump; and a fluid outlet line from the outflow section of the disposable pump, wherein the pump interface includes a rotatable sleeve and the disposable pump includes a mating feature configured to rotate the rotatable sleeve upon the application of a rotary force to the mating feature to lock and unlock the disposable pump to and from the pump console.

23. The pump system of claim 22 wherein the pump console includes a magnet for holding the rotatable sleeve in the locked position.

24. A pump system, comprising:

a pump console housing a push rod, a motor and a transmission for driving the push rod in an axially reciprocal motion, the console including a pump interface;

a disposable pump configured to removably mate with the pump interface by advancing the disposable pump in an axial direction corresponding to the axis of reciprocal motion of the push rod, the disposable pump including a housing having an inflow section defining an inflow chamber, and an outflow section defining an outflow chamber, the inflow section and the outflow section being located side-by-side in the housing, an inflow valve located in the inflow chamber and an outflow valve located in the outflow chamber, the housing defining an internal channel axially aligned with and in fluid communication with the inflow section and the outflow section, and a piston located within the internal channel and configured to mate with the push rod for axial reciprocal movement therewith to pump fluid from the inflow section into the internal channel and from the internal channel into the outflow section;

a fluid inlet line to the inflow section of the disposable pump; and a fluid outlet line from the outflow section of the disposable pump, wherein the piston includes at least one flexible member configured to couple and de-couple the push rod, wherein the only external force required to couple the push rod is an axial force on the piston in a first direction, and the only external force required to de-couple the push rod is an axial force on the piston in a second direction opposite the first direction.

25. A method, comprising:

mating a disposable pump with a pump interface of a pump console;

delivering fluid to an inflow chamber of an inflow section of the disposable pump through a fluid inlet line of the disposable pump;

moving an inflow valve located in the inflow chamber to deliver fluid from the inflow chamber to an internal channel of the disposable pump; and moving an outflow valve locating in an outflow chamber of an outflow section of the disposable pump to deliver fluid from the internal channel to the outflow chamber, the inflow section and the outflow section being located side-by-side and the internal channel being axially aligned with the inflow section and the outflow section;

wherein moving the inflow valve and the outflow valve comprises driving a push rod of the pump console in an axially reciprocal motion to move a piston of the disposable pump, the piston located within the internal channel and mated with the push rod for axial reciprocal movement therewith; and wherein mating the disposable pump with the pump interface comprises advancing the disposable pump in an axial direction corresponding to the axis of reciprocal motion of the push rod causing a sloped wall of the internal channel to act on at least one flexible member of the piston to deflect the at least one flexible member into engagement with the push rod.

26. A method, comprising:

mating a disposable pump with a pump interface of a pump console;

delivering fluid to an inflow chamber of an inflow section of the disposable pump through a fluid inlet line of the disposable pump;

moving an inflow valve located in the inflow chamber to deliver fluid from the inflow chamber to an internal channel of the disposable pump;

moving an outflow valve locating in an outflow chamber of an outflow section of the disposable pump to deliver fluid from the internal channel to the outflow chamber, the inflow section and the outflow section being located side-by-side and the internal channel being axially aligned with the inflow section and the outflow section;

wherein moving the inflow valve and the outflow valve comprises driving a push rod of the pump console in an axially reciprocal motion to move a piston of the disposable pump, the piston located within the internal channel and mated with the push rod for axial reciprocal movement therewith;

wherein mating the disposable pump with the pump interface comprises advancing the disposable pump in an axial direction corresponding to the axis of reciprocal motion of the push rod; and disengaging the piston from the push rod by the application of an axial force applied to the piston by the push rod.

27. A method, comprising:

mating a disposable pump with a pump interface of a pump console;

delivering fluid to an inflow chamber of an inflow section of the disposable pump through a fluid inlet line of the disposable pump;

moving an inflow valve located in the inflow chamber to deliver fluid from the inflow chamber to an internal channel of the disposable pump;

moving an outflow valve locating in an outflow chamber of an outflow section of the disposable pump to deliver fluid from the internal channel to the outflow chamber, the inflow section and the outflow section being located side-by-side and the internal channel being axially aligned with the inflow section and the outflow section;

wherein moving the inflow valve and the outflow valve comprises driving a push rod of the pump console in an axially reciprocal motion to move a piston of the disposable pump, the piston located within the internal channel and mated with the push rod for axial reciprocal movement therewith;

wherein mating the disposable pump with the pump interface comprises advancing the disposable pump in an axial direction corresponding to the axis of reciprocal motion of the push rod; and applying a rotary force to the disposable pump about the axial direction to lock and unlock the disposable pump to and from the pump console.

* * * * *